US009758718B2

(12) United States Patent
Jakobs-Sauter et al.

(10) Patent No.: US 9,758,718 B2
(45) Date of Patent: *Sep. 12, 2017

(54) HIGHLY CONCENTRATED, WATER-FREE AMINE SALTS OF HYDROCARBON ALKOXYSULFATES AND USE AND METHOD USING AQUEOUS DILUTIONS OF THE SAME

(71) Applicant: Sasol Germany GmbH, Hamburg (DE)

(72) Inventors: Britta Jakobs-Sauter, Langenfeld (DE); Uwe Kaltwasser, Marl (DE); Heinz Napierala, Herten (DE); Herbert Koch, Raesfeld (DE); Meinolf Enneking, Herne (DE)

(73) Assignee: Sasol Germany GmbH, Hamburg (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/763,416

(22) PCT Filed: Jan. 24, 2014

(86) PCT No.: PCT/EP2014/000186
§ 371 (c)(1),
(2) Date: Jul. 24, 2015

(87) PCT Pub. No.: WO2014/114459
PCT Pub. Date: Jul. 31, 2014

(65) Prior Publication Data
US 2015/0368550 A1   Dec. 24, 2015

(30) Foreign Application Priority Data

Jan. 25, 2013 (DE) .......................... 10 2013 100 789

(51) Int. Cl.

| | | |
|---|---|---|
| C09K 8/584 | (2006.01) | |
| E21B 43/16 | (2006.01) | |
| C09K 8/86 | (2006.01) | |
| C07C 305/04 | (2006.01) | |
| C07C 211/05 | (2006.01) | |
| C07C 211/07 | (2006.01) | |
| C09K 8/60 | (2006.01) | |
| C08G 65/334 | (2006.01) | |
| C08L 71/02 | (2006.01) | |

(52) U.S. Cl.
CPC .............. *C09K 8/86* (2013.01); *C07C 211/05* (2013.01); *C07C 211/07* (2013.01); *C07C 305/04* (2013.01); *C08G 65/3344* (2013.01); *C08L 71/02* (2013.01); *C09K 8/584* (2013.01); *C09K 8/602* (2013.01)

(58) Field of Classification Search
None
See application file for complete search history.

(56) References Cited

U.S. PATENT DOCUMENTS

| 3,990,515 | A | * | 11/1976 | Wilchester et al. ... C09K 8/584 166/270.1 |
|---|---|---|---|---|
| 4,017,405 | A | | 4/1977 | Holm |
| 4,113,011 | A | | 9/1978 | Bernard |
| 4,265,264 | A | | 5/1981 | Sifferman |
| 4,293,428 | A | * | 10/1981 | Gale ...................... C09K 8/584 166/270.1 |
| 4,477,372 | A | | 10/1984 | O'Lenick |
| 4,703,797 | A | | 11/1987 | Djabbarah |
| 4,886,120 | A | | 12/1989 | Shupe |
| H1818 | H | | 11/1999 | Potgieter et al. |
| 2010/0041576 | A1 | * | 2/2010 | Gutierrez ............ C11D 11/0023 510/237 |
| 2011/0059872 | A1 | | 3/2011 | Weerasooriya |

FOREIGN PATENT DOCUMENTS

| EP | 0003183 | 7/1979 |
|---|---|---|
| EP | 0167337 | 1/1986 |
| EP | 0120550 | 4/1989 |
| EP | 0656416 | 6/1995 |
| GB | 1504789 | 3/1978 |
| GB | 2168095 | 6/1986 |
| WO | WO2009/100298 | 8/2009 |
| WO | WO2009/124922 | 10/2009 |
| WO | WO2011/110502 | 9/2011 |

OTHER PUBLICATIONS

Ammonium Lauryl Ether Sulfate, Zhejang Zanyu Technology Co., Ltd, May 11, 2011.
MARLINAT 242/28, Data Sheet, Sasol, Sep. 15, 2014.
MARLINAT 242/70, Data Sheet, Sasol, Sep. 15, 2014.
TEXAPON, Data Sheet, BASF, Nov. 15, 2013.
"Surfactant Science Series", vol. 56, Anionic Surfactants:, ed. Stache, et al., 1996, Ch. 5, by Xavier Domingo, "Alcohol and Ether Sulfates"—p. 232-237.

* cited by examiner

*Primary Examiner* — Jeffrey Washville
(74) *Attorney, Agent, or Firm* — Bushman Werner, P.C.

(57) ABSTRACT

The present invention relates to highly concentrated, anhydrous amine salts of hydrocarbon polyalkoxy sulfates, wherein the salts are selected from the group of substituted amines, preferably alkanolamines. The products obtained are of low viscosity and pumpable at room temperature. Due to the absence of water, the salts are highly resistant to hydrolysis, even at high temperatures. The invention further relates to the use of the compositions according to the invention in an aqueous dilution for use in oil reservoirs with the aim of achieving enhanced oil production, or for the recovery of hydrocarbons from tar sands or other surfaces or materials provided with hydrocarbon.

25 Claims, No Drawings

HIGHLY CONCENTRATED, WATER-FREE AMINE SALTS OF HYDROCARBON ALKOXYSULFATES AND USE AND METHOD USING AQUEOUS DILUTIONS OF THE SAME

This application is a U.S. national phase of PCT/EP2014/000186, filed Jan. 24, 2014, which claims priority to DE102013100789.9 filed Jan. 25, 2013, the disclosures of which are incorporated herein by reference for all purposes.

The present invention relates to highly concentrated, anhydrous amine salts of hydrocarbon polyalkoxy sulfates, wherein the salts are selected from the group of substituted amines, preferably alkanolamines. The products obtained are of low viscosity and pumpable at room temperature. The salts are very resistant to hydrolysis, even at high temperatures.

The invention further relates to the use of the hydrocarbon polyalkoxy sulfates in aqueous dilution, in particular solutions for use in crude oil reservoirs with the aim of achieving enhanced oil production, such as, for example, for surfactant flooding of underground reservoirs or for the so-called "wettability alteration" (change in the wetting behavior) or for the recovery of hydrocarbons from tar sands or other surfaces or materials provided with hydrocarbon. For the understanding of this invention the term "recovery" also includes the purification of surfaces or materials from hydrocarbons, individually or jointly.

PRIOR ART

The salts of the alkyl polyalkoxy sulfates are used in many different applications such as, for example, as textile and leather auxiliaries, in the metalworking industry, as lubricants or cleaning agents, in cosmetics, as oil and gas field chemicals, as detergents and cleaning agents.

The use of alkyl polyalkoxy sulfates as oil and gas field chemicals is known, for example, from GB 2168095 A. Other examples disclosing alkyl polyalkoxy sulfates containing propoxy groups include WO 2009/124922 and WO 2011/110502 A1, where also the ammonium salts (NH4+) of alkyl polyalkoxy sulfates are mentioned in addition to the alkali and alkaline earth metal salts.

According to the prior art, alkyl polyalkoxy sulfates are prepared by addition of ethylene oxide (EO) and/or propylene oxide (PO) and/or a higher alkylene oxide (AO) of natural and synthetic alcohols by reaction in equimolar amounts with, for example, chlorosulfonic acid or gaseous sulfur trioxide, or other suitable sulfurization agents.

In this context, the sulfuric acid half esters of polyalkoxylates are obtained, which are then neutralized with bases. The bases used for neutralization are added in such concentration in water so that the alkyl polyalkoxy sulfates are obtained as aqueous solutions or pastes. Usually, alkyl polyalkoxy sulfates neutralized with alkali metal hydroxides or ammonia are present in liquid form as aqueous dilution with a concentration of less than 30% by weight. Above 30% by weight the products form highly viscous gel phases. In addition to the high water content of this delivery form, the products are subject to the risk of microbial contamination, which makes the addition of biocide or preservative necessary. There are highly concentrated delivery forms of the alkali salts with an active content of between 70% by weight and in some cases over 80% by weight, the viscosity of which is in a manageable range with respect to pumpability. Such highly concentrated products are increasingly subject to the risk of hydrolysis, which takes place autocatalytically in the acidic pH range. In the hydrolysis, $SO_3$ is released from the molecule, and reacts with water to form sulfuric acid. Due to the resulting sulfuric acid the pH value becomes even lower and further accelerates the hydrolysis.

According to the prior art, the pH value can be kept in a neutral pH range for a limited time by adding suitable buffer substances, so as to delay the hydrolysis.

Elevated temperatures accelerate the decomposition (hydrolysis) of the alkyl polyalkoxy sulfates. Therefore, it is recommended to transport, and also to store the products at temperatures below 30° C., if possible. Warming up products that were exposed to low temperatures again, proves to be very slow because localized overheating must be avoided. Due to the high viscosity in the temperature range around 0° C., the products cannot be pumped or stirred. Local overheating, for example by heating with steam or electrical heating, must be avoided, since this leads to so-called "acidic nests". Local overheating may thus cause the entire storage container to decompose (hydrolyse).

EP 0167337 A2 describes salts of C4 to C10-based alkyl alkoxy sulfates, which can be present also in highly concentrated form as aqueous flowable preparations. In contrast to the above-mentioned salts those with higher alkyl chain lengths are disclosed as being highly viscous.

Surfactant concentrates as base surfactants for concentrated liquid formulations containing alkanolamine salts of alkyl polyethoxy sulfates are known from EP 0656416 A1. The liquid formulations are used as detergents and cleaning agents and are flowable at 70° C.

There is therefore a need for highly concentrated surfactant compositions of the aforementioned type, which are flowable over a wide temperature range and are not, or to a lesser extent, subject to hydrolysis during transport and storage at higher temperatures. At the same time, surfactant compositions are made available that are suitable for use in crude oil production, in particular also at high salinity of the injection water.

SUMMARY OF THE INVENTION

The subject matter of the present is a composition as described in the independent claims. Preferred embodiments are subject of the dependent claims or are described below.

Surprisingly, highly concentrated anhydrous surfactant compositions of alkyl polyalkoxy sulfates were found, which are flowable at 25° C. without addition of solvents. The low risk of hydrolysis enables the storage or transportation at high temperatures and the use of buffer systems to stabilize the pH value is no longer necessary.

The highly concentrated, anhydrous amine salts of the alkyl polyalkoxy sulfates according to the invention can be easily diluted with water. In the process of dilution, the highly viscous gel phases known from the prior art, as they occur in aqueous solutions of alkyl polyalkoxy sulfates neutralized with alkali metal hydroxides or ammonia, are not encountered.

It has surprisingly been found that the aqueous compositions of the above salts, such as those obtainable by diluting the above highly concentrated anhydrous compositions or also by aqueous preparation, have better thermal stability than the corresponding salts of the alkyl polyalkoxy neutralized with alkali metal hydroxides or ammonia salts.

This increased temperature stability in aqueous solution is also found in such amine-neutralized alkyl polyalkoxy sulfates that not in the anhydrous form are flowable and pumpable at room temperature.

Salts of alkyl polyalkoxy sulfates neutralized with alkali metal hydroxides or ammonia having a concentration of, for example, 10% by weight active content in aqueous solution are stable only for a few days at temperatures above 30° C. and hydrolyze completely. Salts of alkyl polyalkoxy sulfates neutralized with amines are stable for several weeks, in some cases several months, at above 30° C. or even higher temperatures, such as, for example, at 70° C., and have lower rates of hydrolysis. Surprisingly it has been found that amine salts of alkyl polyalkoxy sulfates have the same "Optimum Temperature" or "Optimum Salinity" as the corresponding sodium salts. The temperature/salinity, where a water-oil-surfactant system, comprising optionally other additives, reaches the "optimal" Winsor III state is called Optimum Temperature and Optimum Salinity, respectively.

DETAILED DESCRIPTION OF THE INVENTION

The flowable amine salts of the hydrocarbon polyalkoxy sulfates

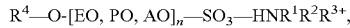

$$R^4\text{—O-[EO, PO, AO]}_n\text{—SO}_3\text{—HNR}^1R^2R^{3+},$$

comprising at least one PO— (propoxy) and at least one EO— (ethoxy) group, hereinafter simplified also called alkyl polyalkoxy sulfate salts, contain one or more primary, secondary or tertiary alkyl and/or alkanol amine compounds as counter ion.

According to one embodiment the present invention concerns a highly concentrated composition flowable at 25° C. comprising:
(A) greater than 80% by weight amine salts of hydrocarbon polyalkoxy sulfates of above formula, in particular greater than 90% by weight, in particular greater than 95% by weight or mixtures thereof;
(B) at least 0.1 up to less than 5% by weight, in particular 0.2 to 3% by weight of the corresponding non-sulfated polyalkoxylated hydrocarbon $R^4$—O-[EO, PO, AO]$_n$—H or of the mixtures thereof;
(C) up to less than 5% by weight of the non-sulfated hydroxy hydrocarbons $R^4$—OH or mixture thereof; and
wherein (B) and (C) together represent 0.1 to 10% by weight, in particular 0.5 to 5% by weight of the composition; and
less than 2% by weight, preferably less than 0.5% by weight water and most preferred less than 0.05% by weight water.

For the purposes of the present invention, the specified numerical values of the alkoxy groups represent always an average (number average).

Suitable protonated alkyl, alkenyl and/or alkanol amines are:

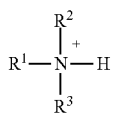

wherein one, two or three of the substituents $R^1$, $R^2$ and $R^3$ are each independently selected from the group:
  alkyl having 1 to 14, in particular 4 to 8 carbon atoms,
  alkenyl having 3 to 18, in particular 4 to 8 carbon atoms,
  hydroxyalkyl having 2, 3 or 4, in particular 3 carbon atoms,
  and mixtures thereof, where the hydroxyalkyl is optionally alkoxylated and where the remaining substituents are hydrogen. Also comprised are mixtures of alkyl polyalkoxy sulfate salts having different alkyl, alkenyl and/or hydroxy alkyl-substituents.

Particularly suitable amine compounds are, for example, mono- or di-ethylamine, mono- or di-butylamine, mono- or di-oleyl amine, mono- or di-2-ethyl hexylamine or other mixtures. Examples of alkanolamines include diethanolamine (DEA), triethanolamine (TEA), monoisopropanolamine (MIPA), diisopropanolamine (DIPA) or triisopropanolamine (TIPA).

$R^4$ represents one or more, optionally different, C6 to C36, C8 to C36 or C10 to C36 hydrocarbon substituents, in particular C12 to C24 hydrocarbon substituents. The underlying alcohols may be, for example, hexanol, heptanol, octanol, nonanol, decanol, undecanol, dodecanol, tridecanol, tetradecanol, pentadecanol, octadecanol, behenyl alcohol, and the corresponding branched, optionally unsaturated types of the same C chain such as, for example, oleyl alcohol, iso-octanol, 2-ethyl-hexanol, 2-hexyldecanol, 2-hexyldodecanol, 2-decyltetradodecanol or isotridecanol and mixtures thereof. The alcohols may be of petrochemical, oleochemical or synthetic origin. Examples of synthetic origin include the Fischer-Tropsch alcohols, Guerbet alcohols, or Ziegler alcohols or alcohols accessible by hydroformylation of the olefins. The alkenes for reaction are available, for example, by metathesis or oligomerization.

Alkylpolyalkoxylates can be prepared from alcohols, in that they are reacted with propylene oxide and optionally ethylene oxide and/or a higher alkylene oxide, in any order. The reaction can be carried out with a single alkylene oxide, or for the production of blocks, with a plurality of alkylene oxides in succession. It is also possible to react mixtures of alkylene oxides of different composition, or to combine the production of blocks with quasi-randomly distributed sequences, as they result from the reaction kinetics.

The number of alkoxy groups EO, PO, and AO is 2 to 30, preferably 2 to 16 or 2 to 16 and most preferably 3 to 16 or 4 to 13, wherein the by-products, which incorporate no alkoxy groups (n=0) do not contribute to the mean value. The alkoxy groups are selected from:
  a) 1 to 16 or 1 to 15, preferably 3 to 15 or most preferably 4 to 13 or 3 to 10 propoxy groups (PO), and
  b) 1 to 15, in particular 1 to 8 or 1 to 3 ethoxy groups (EO),
and optionally additionally
  c) 0 to 10, in particular 0 to 5 or also 1 to 3 higher (C4-C12) alkoxy groups (AO),
and are randomly distributed, are present in blocks, or both. 0 signifies that also none of the above alkoxy groups can be incorporated. In effect, this means that in hydrocarbon polyalkoxy sulfates with mixed alkoxylate groups always at least one propoxy group and one ethoxy group must be incorporated.

The reaction of the alcohol with alkylene oxides is carried out catalytically. Classical bases, such as NaOH, KOH, sodium methoxide, or double metal cyanide (DMC) catalysts can be used as catalysts. Through selective use of the catalysts, product characteristics of the alkyl polyalkoxylates or the alkyl polyalkoxy sulfates can be set, which can be advantageously used in various applications.

The-sulfation of the alkyl polyalkoxylates of fatty alcohol can be done by the conventional methods in a manner known per se for fatty alcohol ether sulfates manner, with the use of falling-film reactors being preferred. Suitable sulfation agents are, for example, oleum, chlorosulfonic acid or, in particular, sulfur trioxide, where, in particular, the latter is used diluted with an inert gas. The resulting sulfuric acid half ester is not stable and must be transferred immediately to a neutralization cycle where it is reacted or neutralized under high shear with corresponding anhydrous amines, in particular, alkanolamines. In the preferred embodiment, the temperature during the neutralization is maintained at 45 to 65° C., in particular 50 to 60° C., at a pH value (with respect to 1% by weight of the product in water) of pH 7.5 to 10 (according to DIN EN 1262:2004).

An anhydrous and optionally solvent-free composition that is flowable at 25° C. (room temperature) is obtained by neutralization with suitable alkyl-/alkanolmine compounds. Preferably, the alkyl polyalkoxy sulfonic acid must be mixed with an equimolar amount or with a slight excess of amine compounds, wherein the pH value is set to a neutral to slightly alkaline value, which is achieved with a 0.1 to 5% by mole excess, preferably 0.1 to 2% by mole excess.

The highly concentrated amine salt of the alkyl polyalkoxy sulfates thus obtained contains smaller proportions of alcohols, alkylene glycols (also sulfated), alkyl polyalkoxylates or also other by-products. The amount of unsulfated material (nonionic substances) in the final product is typically 0.1 to 10% by weight, preferably 0.5 to less than 5% by weight (determined according to DIN EN 13273).

The content of salts of alkyl polyalkoxy sulfates according to the invention in the compositions is greater than 85% by weight, in particular greater than 90% by weight, preferably greater than 95% by weight.

Flowable at 25° C. for the purpose of this invention means that the compositions obtained have a viscosity of less than 20000 mPas, preferably less than 10000 mPas, at a temperature of 25° C. and a shear rate of $D=10\ s^{-1}$. The viscosity is determined according to DIN 53019 using a rheometer with cone/plate measuring geometry. Flowable at a different temperature, e.g. at 15° C. (and above), means for the purpose of the invention that the same values are complied with for the viscosity at a certain different temperature, e.g. at 15° C.

If it is desired to further reduce the viscosity of the alkyl-/alkanolamine salts of the alkyl polyalkoxy sulfates, suitable solvents (except water) such as, for example glycols, e.g., ethanediol, 1,2-propanediol, and other polyols or mixtures thereof can be added.

To determine the storage stability (hydrolytic stability), the products are filled into glass containers, the supernatant headspace is flushed with nitrogen and sealed airtight. Several sealed containers filled with one of the products are stored at the appropriate temperatures in a commercial heating cabinet. After a certain time, the containers are removed, and the pH change and the acid number, by titration in mg KOH/g, are determined When stored above 50° C. or even 70° C. for a storage time of 3 months, or even 6 months, the anhydrous amine salts of the alkyl polyalkoxy sulfates according to the invention show no decrease of the pH value below 6, consequently, a particularly good hydrolytic stability. By contrast, aqueous salts of the alkyl polyalkoxy sulfates neutralized with alkali metal hydroxide solutions and ammonia are subject to hydrolysis upon storage at 30° C. already after 7 to 14 days; within this time the pH drops to a value below pH 3, in some cases below pH 2.

The highly concentrated, anhydrous and optionally solvent-free amine salts of the alkyl polyalkoxy sulfates according to the invention can be easily diluted with water. Surprisingly, during the dilution process there are no highly viscous gel phases as is the case in diluting 70% aqueous preparations of alkyl polyalkoxy sulfates neutralized with alkali metal hydroxides or ammonia.

The dilution of the highly concentrated, anhydrous amine salts of the alkyl polyalkoxy sulfates according to the invention with water is particularly rapid at 35 to 45° C., in particular about 40° C., and associated with low energy input, i.e., easily carried out with stirring at low shear rate. This represents a significant advantage making the use of expensive dilution systems or special mixers superfluous.

To determine the thinnability, the product is mixed at 25° C. with water in ratios yielding corresponding solutions with defined anionic active contents. This is accomplished by the addition of surfactant to distilled water at 25° C. with stirring by hand with a spatula or a glass rod. If this is done without highly viscous gel phases being formed that can no longer be stirred or mixed manually, the product is, according to definition, readily dilutable.

The low pour point of below 10° C., in particular below 0° C., allows the storage or also the transport at low temperatures maintaining the flowable state. The pour point of the alkyl/alkanolamine salts of the alkyl polyalkoxy sulfates according to the invention is determined according to ASTM D97-09, by cooling the product in steps of 3° C. If after 10 minutes at a certain temperature the product does not flow within 5 seconds after tilting the container in the horizontal position, the 3° C. higher value is the pour point.

Due to their higher stability, in particular temperature stability, compared with the alkali metal or ammonium salts, the highly concentrated, anhydrous and optionally solvent-free amine salts of the alkyl polyalkoxy sulfates according to the invention, following dilution with water, can be used advantageously for application in crude oil reservoirs with the aim of achieving enhanced oil production, such as, for example, for surfactant flooding of underground reservoirs or for the so-called "wettability alteration" (change in the wetting behavior) or for the recovery of hydrocarbons from tar sands or other surfaces or materials provided with hydrocarbon.

This increased temperature stability in aqueous solution is also found in such amine-neutralized alkyl polyalkoxy sulfates that not in the anhydrous form are flowable and pumpable at room temperature. These are also suitable for application in oil reservoirs with the aim of achieving enhanced oil production, or for the recovery of hydrocarbons from tar sands or other surfaces or materials provided with hydrocarbon.

Primary crude oil production refers to the production of crude oil by the inherent pressure in the reservoir. Depending on the reservoir, often only about 5 to 10% of the crude oil present in the reservoir can be produced by means of the primary production until the inherent pressure is no longer sufficient for production.

In secondary production, fluid is injected into the reservoir in order to maintain the pressure or to increase it again. By injecting the water through so-called injection wells, the crude oil is slowly pushed through the hollow spaces in the formation toward the production well. As long as the cavities are completely filled with oil, the more viscous oil is pushed by the water in front of the water. Once the low-viscous water breaks through cavities, it flows from this point on the path of least resistance, i.e. through the channel formed, and no longer pushes the oil in front of it. The different polarity of oil and water provides for a high surface energy or interfacial tension. Therefore, both assume the smallest contact area with each other, resulting in a spherical oil droplet, which no longer fits through the fine capillaries of the reservoir. The oil is trapped in the capillaries in discontinuous form (isolated spherical drops). As a rule, primary and secondary production can produce only about 20 to 40% of the crude oil present in the reservoir.

Enhanced Oil Recovery (abbreviated EOR) or Improved Oil Recovery (abbreviated IOR) or in the German language "tertiäre Erdölförderung [tertiary crude oil recovery]", hereinafter in brief (together) called EOR, refers to techniques for increasing the amount of crude oil that can be extracted from a reservoir, for example, an oil field. EOR may also be referred to as enhanced oil recovery in comparison with a merely primary or a primary and secondary oil recovery. Using EOR, typically about 40%-60% of crude oil remaining after primary production can be extracted from the reservoir.

EOR can be achieved through a variety of methods, such as miscible gas injection (including carbon dioxide injection), chemical injection (including polymer flooding and/or alkaline flooding and/or surfactant flooding or combinations thereof, including "wettability alteration" (changing the wettability of rock surfaces), and carbon dioxide foam, microbial injection, or thermal "Recovery" (which includes cyclic steam injection), steam flooding, and fire flooding. Furthermore, oil or tar sands, for example, or other oil-wetted surfaces can be de-oiled by treatment with aqueous solutions of the amine-neutralized alkyl polyalkoxy sulfates.

The injection of alkaline aqueous solution in reservoirs, the crude oil of which contains naturally occurring organic acids, results in the formation of soaps. These soaps decrease the interfacial tension and thus can increase the production. Some crude oils contain carboxylic acids having, for example, C11 to C20 alkyl chains, naphthenic acids, and others. An improvement of the production of such "reactive" oils can be achieved by using alkali (for example, NaOH or $Na_2CO_3$) in a surfactant composition. Injection of a dilute solution of a water-soluble polymer which increases the viscosity of the injected water and adapts it to the viscosity of the crude oil in the formation may increase the production of oil from geological formations of sufficient permeability.

For low permeability reservoirs ("tight formations"), on the other hand, for example, the method of so-called "wettability alteration" lends itself to extended crude oil production. In this case, the wettability of the rock is changed from oil-wetted to water-wetted using surfactants, which are injected in a dilute aqueous solution, whereby additional oil is mobilized.

Viscous and capillary forces act on the crude oil, wherein the ratio of these two forces to each other determines the microscopic oil separation. The action of these forces is described by means of a dimensionless parameter, the so-called capillary number N. It is the ratio of the viscous forces (velocity×viscosity of the pushing phase) to the capillary forces (interfacial tension between oil and water×wetting of the rock):

$$N=\mu V/\sigma \cos\theta$$

$\mu$ is the viscosity of the fluid mobilizing the crude oil, V is the Darcy velocity (flow per unit area), $\sigma$ is the interfacial tension between the fluid mobilizing the crude oil and the crude oil, and $\theta$ is the contact angle between crude oil and the rock (C. Melrose, C F. Brandner, J. Canadian Petr. Techn. 58, Oct. Dec. 1974). The higher the capillary number, the greater the mobilization of the oil and thus the degree of de-oiling.

It is known that the capillary number towards the end of the secondary crude oil production is in the range of about $10^{-6}$ and that it is necessary to increase the capillary number to about $10^{-3}$ to $10^{-2}$ in order to be able to mobilize additional crude oil.

It is possible, for example, to lower the interfacial tension $\sigma$ between the crude oil and the aqueous phase by the addition of suitable surfactants, also known as "surfactant flooding". Particularly suitable surfactants for this purpose are those which can lower $\sigma$ to values of no more than 0.01 mN/m (ultralow interfacial tension).

Special formulations of surfactants with water and oil form a microemulsion (Winsor type III). The occurrence of certain phase states is determined by internal (composition) and external parameters (such as temperature and salinity), the latter being usually dictated by the geological conditions in an oil reservoir. The Winsor III phase state, also called three-phase microemulsion (the actual microemulsion being the middle phase, accompanied by a water and an oil excess phase), is characterized by extremely low interfacial tensions (IFT). Therefore, this state is also called "Optimal", and the associated parameters as the "Optimum Salinity" or "Optimal Temperature".

Surprisingly, the amine salts of alkyl polyalkoxy sulfates show with respect to the EOR application the same OS*/OT*pairs (OT*=Optimal Temperature, OS*=Optimal salinity) as the corresponding sodium salts, i.e., at the same reservoir conditions they reach the optimum condition with ultralow interfacial tension. The middle phase is usually of low viscosity. A low viscosity is desirable for transport of the emulsion in the crude oil formation.

Typical reservoir temperatures are about 30° C. to about 130° C. in the presence of water containing high concentrations of salt. When the available water is rich in calcium and magnesium ions, the alkali added may cause a precipitation of cations, such as $Ca^{+2}$ or $Mg^{+2}$. In order to prevent such precipitation, it is necessary to add chelating agents such as, for example, EDTA to the surfactant composition. Alternatively, water softening processes can be used to process the injection water. Alternatively, surfactants may also be used that are soluble in reservoir water with high salt content (water for injection).

For application in tertiary crude oil recovery, a high long-term stability of the surfactants under reservoir conditions is necessary because the migration velocity in the formation is often less than 1 m/day. Depending on the distance between the injection and production wells the residence times of the surfactant in the crude oil reservoir can be several months.

EXPERIMENT EXAMPLES

Example a)

A linear C10 alcohol is reacted with KOH as catalyst and 4 moles of propylene oxide and 1 mol of ethylene oxide at temperatures of 130-165° C. and a pressure range of 2 to 3 bar in a stirred autoclave. The resulting alkoxide (4 PO+1 EO) was sulfated in a continuous sulfation apparatus (falling film reactor from BALLESTRA). Gaseous $SO_2$ was converted to $SO_3$ at a $V_2O_5$ catalyst at high temperature. The gas was cooled and diluted with air (dew point −60° C.).

The alkoxylated alcohol was reacted with the $SO_3$/air mixture in a falling film reactor with a distributor. The reaction gas flows through the falling film reactor at high velocity and generates high turbulences upon contact with the propoxylated alcohol. This generated an intensive mass exchange. Intensive cooling of the falling film reactor provides for the removal of the heat of reaction. The gas/liquid separation was performed at the outlet of the falling film reactor. The liquid phase enters into the neutralization, the gas phase into the exhaust gas processing.

MIPA as a neutralizing agent was continuously fed in stoichiometric amounts. At the same time, the product is homogenized in circulation with a high-shear mixing tool. The finished product was removed continuously from the neutralizing circulation. Examples b-d were prepared according to the experimental description above and are reacted to form the corresponding alcohol propoxy sulfate salts:

b) a Sulfate of a Linear C10 Alcohol having on Average 4 PO and 1 EO Groups with TIPA, According to the above experimental description the following compounds/compound mixtures were prepared as comparative examples:

c) a Sulfate of a Branched C24 Alcohol (ISOFOL® 24) (without PO Groups) with MIPA, and d) a Sulfate of a Branched C24 Alcohol (ISOFOL® 24) (without PO Groups) with TIPA.

TABLE 1

| Example | Anionic active substance (% by weight) | Unsulfated matter (% by weight) | Amine-Sulfate (% by weight) | Free Amine (% by weight) | pH 1% in water | Viscosity (mPas, 25° C. and 10 s−1) |
|---|---|---|---|---|---|---|
| a) | 98.1 | 0.8 | 0.6 | 0.5 | 8.6 | 2100 |
| b) | 95.4 | 1.3 | 0.9 | 2.4 | 7.8 | 6300 |
| c) | 95 | 3.1 | 1.7 | 0.2 | 8.3 | solid |
| d) | 90.8 | 5.1 | 3.8 | 0.3 | 7.8 | 75000 |

Analogous compounds which have been neutralized with NaOH instead of the amines according to the invention and then dehydrated, are solids at 25° C. The resulting compositions and properties are shown in Table 1 below.

Table 2 shows the pH values of 10% aqueous solutions of the listed compounds determined before and after storage at 70° C. The extent of the pH decrease is an indication of hydrolysis.

TABLE 2

| Composition | Start pH value | 70° C. storage time | pH value |
|---|---|---|---|
| according to example a) | 8.7 | 6 months | 7.2 |
| according to example b) | 7.9 | 6 months | 7.7 |

In order to evaluate the long-term stability under simulated use conditions, compositions were prepared as follows each with:

1% surfactant based on active matter in demineralized water
+0.1% polymer "Flopaam® 3330 S" (SNF SAS—France)
+2% NaCl whereupon the pH value was adjusted to pH 10.0 with NaOH or $Na_2CO_3$, the composition was kept at a defined temperature over the specified time interval and the pH value was determined as a measure for the decomposition of the alkyl polyalkoxy sulfates/alkoholether sulfates.

The results are shown in table 3.

TABLE 3

| | amine and/or salt | 70° C. $Na_2CO_3$ (pH value at the beginning: 10.0) |
|---|---|---|
| Sulfate of a linear C10 Ziegler alcohol with an average of 4 PO and 1 EO group | Na MIPA TIPA | after 3 weeks pH 5.7 after 6 months pH 9.7 after 6 months pH 9.8 |

The invention claimed is:

1. A highly concentrated composition of amine salts of hydrocarbon polyalkoxy sulfates that is flowable at 25° C., comprising:
   (A) greater than 80% by weight, amine salts of hydrocarbon polyalkoxy sulfates of the formula $R^4$—O—[EO, PO, AO]$_n$—$SO_3$—$HNR^1R^2R^{3+}$ wherein at least one of substituents $R^1$, $R^2$ and $R^3$ is a hydroxyalkyl having 2 to 4 carbon atoms,
   wherein
   one or two of substituents $R^1$, $R^2$ and $R^3$ are each independently selected from the group:
      alkyl having 1 to 14 carbon atoms,
      alkenyl having 3 to 18 carbon atoms,
      hydroxyalkyl having 2 to 4 carbon atoms,
      and mixtures thereof
   wherein the hydroxyalkyl is optionally alkoxylated and
   wherein any remaining substituent(s) are each hydrogen; and
   $R^4$ is/are one or more different C6 to C36 hydrocarbon(s),
   optionally in a mixture with less than 20% by weight of the above amine salts of hydrocarbon polyalkoxy sulfates in which the alkoxy groups are exclusively EO;
   (B) at least 0.1 up to less than 5% by weight of the non-sulfated polyalkoxylated hydrocarbon $R^4$—O—[EO, PO, AO]$_n$—H or of the mixture;
   (C) up to less than 5% by weight of the non-sulfated hydroxy hydrocarbons $R^4$—OH or of the mixture;
   wherein (B) and (C) together represent 0.1 to 10% by weight of the composition;
   wherein the composition
   comprises less than 2% by weight of water and
   wherein the number n of the alkoxy groups EO, PO, AO combined is 2 to 16,
   and the alkoxy groups are selected from:
   1 to 15 propoxy groups (PO) and
   1 to 15 ethoxy groups (EO),
   and optionally
   0 to 10 C4 to C12-alkyleneoxy groups (AO),
   and the alkoxy groups are distributed randomly or are present in blocks, or both.

2. The composition according to claim 1, wherein $R^4$ is one or more different C8 to C36 hydrocarbon(s).

3. The composition according to claim 1, wherein two or three of the substituents $R^1$, $R^2$ and $R^3$ are hydroxyalkyl each having 2 and/or 3 carbon atoms and any remaining substituents are each hydrogen, wherein the C2 or C3 hydroxyalkyl optionally is alkoxylated.

4. The composition according to claim 1, wherein one, two or three of the substituents $R^1$, $R^2$ and $R^3$ each are isopropanol, and any remaining substituents are each hydrogen, wherein the isopropanol optionally is alkoxylated.

5. The composition according to claim 1, wherein the number n of the alkoxy groups EO, PO, AO combined is 3 to 16.

6. The composition according to claim 1, wherein the EO, PO, AO alkoxy groups are selected independently from each other from:
4 to 13 propoxy groups (PO),
1 to 8 ethoxy groups (EO), and
0 to 5 C4 to C12 alkyleneoxy groups (AO), and the alkoxy groups are distributed randomly or are present in blocks, or both.

7. The composition according to claim 1, wherein the composition essentially consists out of the components (A) to (C) and optionally water.

8. The composition according to claim 1, comprising less than 0.5% by weight water.

9. The composition according to claim 1, further comprising (D) up to 5% by weight of non-sulfated amine or of the amine mixture $NR^1R^2R^3$.

10. The composition according to claim 1, further comprising
(E) 0.1 to 5% by weight of the sulfate of the amine or of the amine mixture $(HNR^1R^2R^3)_2SO_4$.

11. The composition according to claim 10, further comprising
(F) 0.1 to 5% by weight

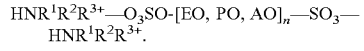
$HNR^1R^2R^{3+}$.

12. The composition according to claim 1, further comprising 0.05 to 10% by weight of the sulfated non-alkoxylated hydroxy hydrocarbon $R^4$—O—$SO_3$—$HNR^1R^2R^{3+}$ or mixtures.

13. The composition according to claim 1, wherein the composition is flowable at 15° C. and above.

14. The composition according to claim 1, wherein the composition has a pour point of less than +5° C.

15. The composition according to claim 1, comprising in total less than 10% by weight of other nonionic surfactants than those mentioned in the above mentioned claims.

16. The composition according to claim 1, further comprising in total less than 5% by weight of solvent or diluent.

17. A method of supporting production of crude oil, said method comprising: introducing aqueous compositions comprising from 0.05 to 5% by weight of hydrocarbon polyalkoxy sulfates of the formula $R^4$-[EO, PO, AO]$n$—O—$SO_3$—$HNR^1R^2R^{3+}$ wherein
the number n of the alkoxy groups EO, PO, AO combined is 2 to 30,
and the alkoxy groups are selected from:
1 to 15 propoxy groups (PO) and
1 to 15 ethoxy groups (EO),
and optionally
0 to 10 C4 to C12 alkyleneoxy groups (AO),
and the alkoxy groups are distributed randomly or are present in blocks, or both; and
at least one of substituents $R^1$, $R^2$ and $R^3$ is a hydroxyalkyl having 2 to 4 carbon atoms, one or two of the substituents $R^1$, $R^2$ and $R^3$ are each independently selected from the group consisting of
alkyl having 1 to 14 carbon atoms,
alkenyl having 3 to 18 carbon atoms,
hydroxyalkyl having 2 to 4 carbon atoms,
and mixtures thereof
wherein the hydroxyalkyl is optionally alkoxylated,
wherein any remaining substituents are each hydrogen, and
$R^4$ is one or more different C6 to C36 hydrocarbons,
into underground crude oil reservoirs to support the production of crude oil.

18. The method according to claim 17, wherein $R^4$ is one or more different C8 to C36 hydrocarbon(s).

19. The method according to claim 17, wherein one, two or three of the substituents $R^1$, $R^2$ and $R^3$ are hydroxyalkyl each having 2 and/or 3 carbon atoms and any remaining substituent are each hydrogen, wherein the C2 or C3 hydroxyalkyl optionally is alkoxylated.

20. The method according to claim 17, wherein one, two or three of the substituents $R^1$, $R^2$ and $R^3$ each are isopropanol, and any remaining substituents are each hydrogen, wherein the isopropanol optionally is alkoxylated.

21. The method according to claim 17, wherein the number n of the alkoxy groups EO, PO, AO combined is 3 to 16.

22. The method according to claim 17, wherein the EO, PO, AO alkoxy groups are selected independently from each other from:
4 to 13 propoxy groups (PO),
1 to 8 ethoxy groups (EO), and
0 to 5 C4 to C12 alkyleneoxy groups (AO),
and the alkoxy groups are distributed randomly or are present in blocks, or both.

23. The method according to claim 17, wherein the compositions comprise 0.1% per weight to 3% per weight of the hydrocarbon polyalkoxy sulfates.

24. The method according to claim 17, wherein the underground crude oil reservoirs have reservoir temperatures of the to be treated reservoir from 0° C. to 100° C.

25. The method according to claim 17, wherein the underground crude oil reservoirs have reservoir temperatures of the treated reservoir having a maximum of above 75° C. to 110° C.

* * * * *